(12) United States Patent
Godlewski

(10) Patent No.: US 11,568,363 B2
(45) Date of Patent: *Jan. 31, 2023

(54) PORTABLE INVENTORY TRACKING SYSTEM

(71) Applicant: CareFusion 303, Inc., San Diego, CA (US)

(72) Inventor: Peter Godlewski, San Clemente, CA (US)

(73) Assignee: CareFusion 303, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/527,045

(22) Filed: Nov. 15, 2021

(65) Prior Publication Data

US 2022/0076198 A1 Mar. 10, 2022

Related U.S. Application Data

(63) Continuation of application No. 16/867,493, filed on May 5, 2020, now Pat. No. 11,176,515, which is a
(Continued)

(51) Int. Cl.
*G06Q 10/08* (2012.01)
*G16H 20/13* (2018.01)
*G06Q 50/28* (2012.01)

(52) U.S. Cl.
CPC ....... *G06Q 10/087* (2013.01); *G06Q 10/0875* (2013.01); *G06Q 50/28* (2013.01); *G16H 20/13* (2018.01)

(58) Field of Classification Search
CPC ... G06Q 10/087; G06Q 10/0875; G06Q 50/28
See application file for complete search history.

(56) References Cited

U.S. PATENT DOCUMENTS

| 5,905,653 A | 5/1999 | Higham et al. |
| 6,011,999 A | 1/2000 | Holmes |

(Continued)

FOREIGN PATENT DOCUMENTS

| CN | 1781423 A | 6/2006 |
| CN | 101322151 A | 12/2008 |

(Continued)

OTHER PUBLICATIONS

W. Yao, C.-H. Chu and Z. Li, "The use of RFID in healthcare: Benefits and barriers," 2010 IEEE International Conference on RFID—Technology and Applications, 2010, pp. 128-134. (Year: 2010).*

(Continued)

*Primary Examiner* — Asfand M Sheikh
(74) *Attorney, Agent, or Firm* — Morgan, Lewis & Bockius LLP

(57) ABSTRACT

A system and method for managing inventory in a dispensing cabinet includes a mobile terminal, and an association station configured to associate the mobile terminal with an item type stored in the dispensing cabinet. The association station receives, from the mobile terminal, an indication of a respective item unit of the first item type being moved, determines an access status of one or more containers of the dispensing cabinet when the indication is received, determines a container location for the item unit based on the access status of the containers and receiving the indication of the respective item being moved from the first mobile terminal, and causes, responsive to determining the container location, a supply record associated with the item type and a first container of the dispensing cabinet to be updated to reflect a change to a first amount of the first item type stored in the first container.

20 Claims, 9 Drawing Sheets

Related U.S. Application Data continuation of application No. 12/503,012, filed on Jul. 14, 2009, now Pat. No. 10,657,488.

(56) References Cited

U.S. PATENT DOCUMENTS

| | | | |
|---|---|---|---|
| 6,105,004 | A | 8/2000 | Halperin et al. |
| 6,151,538 | A | 11/2000 | Arnold et al. |
| 6,223,163 | B1 | 4/2001 | Van Luchene |
| 6,430,689 | B1 | 8/2002 | Lacombe et al. |
| 6,801,877 | B2 | 10/2004 | Schiltz et al. |
| 6,959,862 | B2 | 11/2005 | Neumark |
| 6,993,501 | B1 | 1/2006 | Zhao |
| 7,072,855 | B1 | 7/2006 | Godlewski et al. |
| 7,084,738 | B2 | 8/2006 | Bastian, II |
| 7,146,247 | B2 | 12/2006 | Kirsch et al. |
| 7,212,098 | B1 | 5/2007 | Trent |
| 7,348,884 | B2 | 3/2008 | Higham |
| 7,463,947 | B1 | 12/2008 | Frederick et al. |
| 7,630,791 | B2 * | 12/2009 | Nguyen .............. A61B 90/96 700/242 |
| 7,639,136 | B1 | 12/2009 | Wass et al. |
| 8,749,382 | B2 | 6/2014 | Sterzinger |
| 2004/0207512 | A1 | 10/2004 | Bastian, II |
| 2006/0022827 | A1 * | 2/2006 | Higham ............. G08B 13/2417 340/572.1 |
| 2006/0136167 | A1 | 6/2006 | Nye |
| 2006/0232412 | A1 | 10/2006 | Tabacman |
| 2007/0135965 | A1 | 6/2007 | Nguyen et al. |
| 2007/0208454 | A1 | 9/2007 | Forrester et al. |
| 2007/0272746 | A1 | 11/2007 | Ortiz et al. |
| 2008/0091574 | A1 | 4/2008 | Hamaji |
| 2008/0249899 | A1 | 10/2008 | Nasser |
| 2008/0297314 | A1 | 12/2008 | Kuwako et al. |
| 2009/0021345 | A1 * | 1/2009 | Sriharto ............. G08B 13/1427 340/5.6 |

FOREIGN PATENT DOCUMENTS

| | | |
|---|---|---|
| JP | 2008299468 A | 12/2008 |
| KR | 20030052675 A | 6/2003 |

OTHER PUBLICATIONS

Australian Examination Report No. 1 for Application No. 2010273548, dated Aug. 13, 2015, 4 pages.
Australian Examination Report No. 2 for Application No. 2010273548, dated Dec. 11, 2015, 4 pages.
Australian Examination Report No. 4 for Application No. 2010273548, dated Jun. 3, 2016, 4 pages.
Australian Examination Report No. 5 for Application No. 2010273548, dated Jul. 26, 2016, 4 pages.
Becker, Eric, et al., "SmartDrawer: RFID smart medicine drawer for assistive environments," Proceedings of the 2nd International Conference on Pervasive Technologies Related to Assistive environments, ACM, 2009.
Brazil Office Action for Application No. 112012000331-3, dated Nov. 4, 2019, 7 pages.
Canadian Office Action for Application No. 2767334, dated Jul. 13, 2016, 4 pages.
Canadian Office Action for Application No. 2767334, dated Jul. 3, 2018, 5 pages.
Canadian Office Action for Application No. 2767334, dated Jul. 5, 2017, 4 pages.
Canadian Office Action for Application No. 2767334, dated Jun. 20, 2019, 5 pages.
Chinese Office Action for Chinese Application No. 201080031687.5, dated Apr. 8, 2014, 10 pages.
English language translation of Korean Office Action for Application No. 1020187016573, dated Aug. 31, 2018, 4 pages.
English language translation of Korean Office Action for Application No. 1020187016573, dated May 15, 2019, 3 pages.
European Office Action for European Application No. 10736923.3, dated Mar. 3, 2015, 7 pages.
Extended European Search Report for European Application No. 10736923.3, dated Jul. 4, 2014, 7 pages.
Indian Office Action for Application No. 189/CHENP/2012, dated Jul. 15, 2019, 6 pages.
International Preliminary Report on Patentability for International Application No. PCT/US2010/041820, dated Jan. 16, 2012, 5 pages.
International Search Report and Written Opinion for International Application No. PCT/US2010/041820, dated Apr. 27, 2011, 6 pages.
Korean Office Action for Application No. 10-2012-7001110, dated Aug. 19, 2016, 7 pages excluding translation.
Korean Office Action for Application No. 10-2012-7001110, dated Feb. 14, 2014, 4 pages.
Korean Office Action for Application No. 10-2012-7001110, dated Jun. 16, 2016, 8 pages excluding translation.
Korean Office Action for Application No. 1020177020057, dated Jan. 22, 2018, 4 pages excluding English translation.
Korean Office Action for Application No. 10-2017-7020057, dated Jul. 28, 2017, 9 pages excluding translation.
Korean Office Action for Application No. 10-2018-7016573, dated Mar. 20, 2019, 7 pages.
New Zealand Examination Report for New Zealand Application No. 597456, dated Nov. 8, 2012, 2 pages.
Office Action issued by the Chinese Patent Office for Chinese Application No. 201080031687.5, office action dated Dec. 12, 2014.
Brazil Office Action for Application No. BR112012000331-3, dated Aug. 22, 2020, 9 pages.
Brazil Office Action for Application No. 112012000331-3, dated Apr. 17, 2020, 7 pages.
Shieh, Shien-Chii, et al. "Using RFID technology on clinic's pharmacy operation management and development of intelligent medicine dispensing cabinet." 2008 IEEE International Conference on Industrial Engineering and Engineering Management. IEEE, 2008.

* cited by examiner

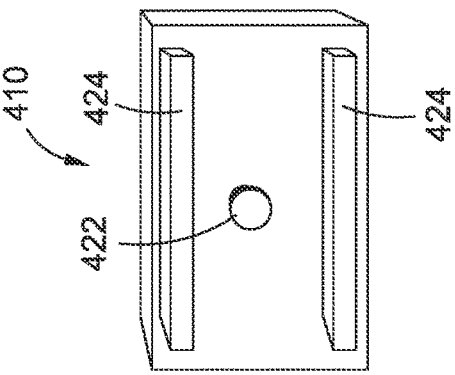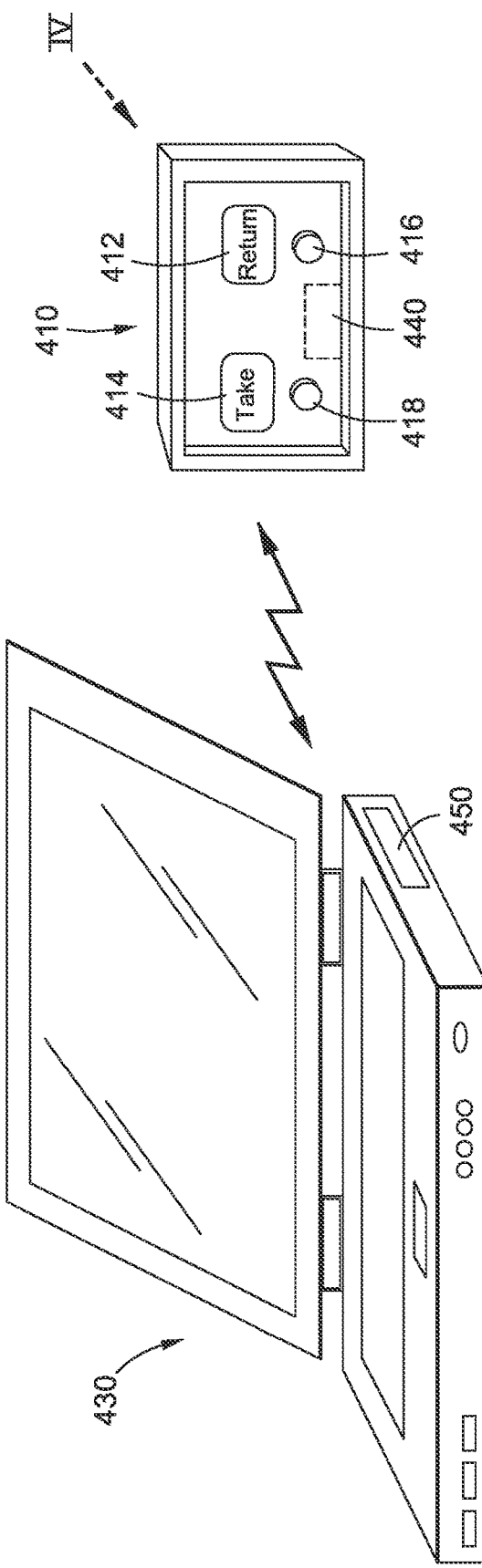

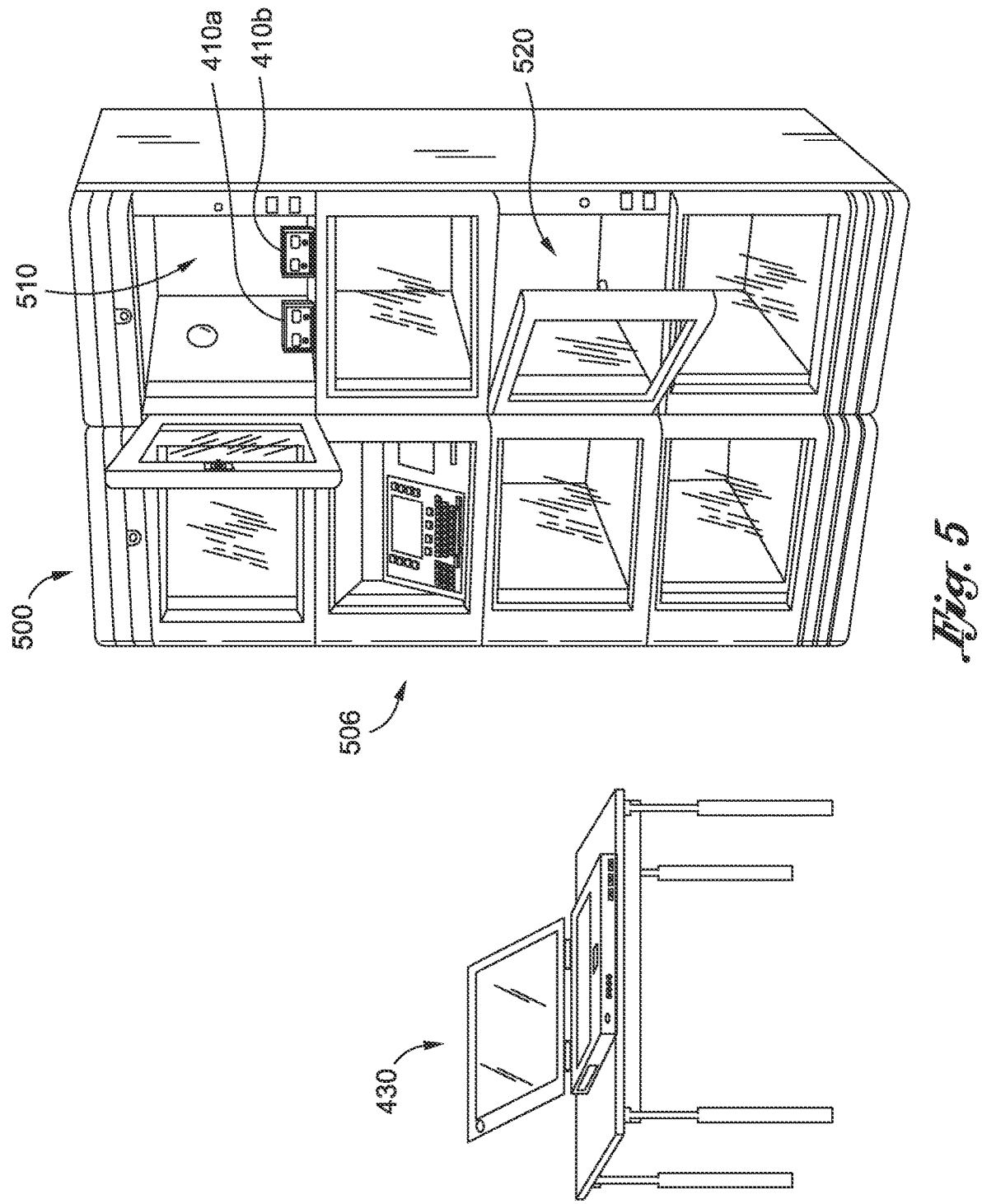

PORTABLE INVENTORY TRACKING SYSTEM

CROSS-REFERENCE TO RELATED APPLICATIONS

This application is a continuation application of U.S. application Ser. No. 16/867,493, entitled "PORTABLE INVENTORY TRACKING SYSTEM," filed on May 5, 2020, which is a continuation application of U.S. application Ser. No. 12/503,012, entitled "PORTABLE INVENTORY TRACKING SYSTEM," filed on Jul. 14, 2009, now U.S. Pat. No. 10,657,488, the entirety of each of which is incorporated herein by reference.

BACKGROUND

Field

The present disclosure generally relates to item tracking devices, and more particularly, to tracking a quantity of items.

Description of the Related Art

It is well known in the medical community, and in particular, in hospitals, to provide centrally located medication and supply dispensing stations, such as cabinet 100 illustrated in FIG. 1. Such generally accessible cabinets 100 serve several functions including providing a centralized distribution point of medicines and supplies to patients.

Some of these cabinets 100 include hardwired buttons (e.g., physically connected to a circuit assembly of the station) in order to track quantities of supplies within the station. For example, the cabinet 100 includes a return button 102 and a take button 104, indicating to the cabinet's computer system 106 the removal or addition, respectively, of an item from an inventory for the item in a container 110 (e.g., a shelf). These buttons 102 and 104 require multiple manual interactions by a user to be associate the actions triggered by the buttons 102 and 104 with items in the cabinet 100.

For example, when a user wants to add a new item to the inventory housed in the cabinet 100, it usually requires a minimum of nine steps. Specifically, as illustrated in the process 200 of FIG. 2, in step 201, a user would first need to log in to the computer system 106 of the cabinet 100 to place the cabinet 100 into a mode that recognizes that the user intends to load a supply of items in the container 110 and assign buttons 102 and 104 to the item. Next, in step 202, the user opens the container 110 to access the space within the container, in step 203, the user loads the supply of items in the container 110, and in step 204, selects the buttons 102 and 104 to associate the actions triggered by the buttons 102 and 104 with a change in the supply of the item in the container 110. In step 205, the user selects a description for the item and a quantity of the item (e.g., indicating the supply) to associate with the buttons 102 and 103, and confirms the selection in step 206. In decision step 207, if the user decides to associate another item to other buttons, the process 200 returns to step 203, otherwise the user in step 208 decides whether there are more containers 110 in the cabinet 100 to load with a supply of another item. If there are more containers to load with a supply of another item, the process 200 proceeds to step 209, in which the current container is closed, and another container that is to be loaded with the supply of the other item is opened, and then the process 200 returns to step 203. Otherwise, if there are no more containers to load with a supply of another item, the process moves to final step 210, in which the user logs out of the computer system 106 of the cabinet 100.

By way of another example, when a user wants to reorganize items housed in a container in a cabinet, or add a different item to a fully stocked cabinet, it usually requires a minimum of fourteen steps that include requiring a user to disassociate an item from a pair of buttons and then re-associate the item with another pair of buttons. Specifically, as illustrated in the process 300 of FIG. 3, in step 301, a user would first need to log in to the computer system 106 of the cabinet 100 to place the cabinet 100 into a mode that recognizes that the user intends to reorganize items in the container 110 and reassign different buttons 102 and 104 to the item. Next, in step 302, the user opens the container 110 to access the space within the container, in step 303, the user unloads the supply of items from a location in the container 110, in step 304, selects the buttons 102 and 103 to disassociate from the supply of the item in the container 110, and in step 305, confirms the selection. In decision step 306, if the user wants to disassociate another item in the container 110 from buttons, the process 300 returns to step 304, otherwise the process proceeds to step 307.

In step 305, the user reloads the items unloaded in step 303 to a new location in the container 110, and in step 308 selects a new pair of buttons (associated with the new location)) for the same container 110 to associate with the supply of the item. In step 309, the user selects a description for the item and a quantity of the item (e.g., indicating the supply) to associate with the new pair of buttons 102 and 103, and confirms the selection in step 310. In decision step 311, if the user decides that no other items need to be associated with a new pair of buttons (i.e., no other items were selected to be reorganized in steps 303-306), the process 300 proceeds to decision step 312, otherwise the process 300 returns to step 308. In decision step 312, if the user decides to load (e.g., reorganize) items in another container, then in step 313 the user closes the current container 110 and opens another container, and then the process 300 returns to step 303, otherwise, if the user decides not to load (e.g., reorganize) items in another container, the process 300 proceeds to step 314 in which the current open container 110 is closed, and then in step 315, the user logs out of the computer system 106 of the cabinet 100.

Additionally, adding new stock to the cabinet 100 is a distinct process from restocking or reorganizing the cabinet 100 when such stock exceeds space provided in the cabinet 100. Specifically, a user performing a restock of an item has to establish a button association with the item prior to restocking the item in the cabinet 100. On the other hand, if the user wants to add a new item to the cabinet, the user must use a completely separate process Consequently, current cabinets 100 are difficult to reorganize, causing inefficiencies in both cabinet space utilization and responsiveness to changes in inventory quantity and selection. Inventory in a container 110 is rarely static as a new supply of items takes the place of other supplies over time, and inventory optimization efforts cause the required container space for each item to change. In these cases, replacing one item requires the reorganization of many items on the shelves, making the process 300 longer. As illustrated above, for each movement of an item, the user must remove the association of the item to its buttons and re-associate the item to another set of buttons. Even the allocation of additional space in a container for more stock of one item can cause the user to perform re-associations for several items displaced by reorganization. For example, it is not unusual for a user to have to move multiple items to accommodate a single new item or an increase in stock for an item. Consequently, reconfiguration and optimization of container space often takes several days.

As a simple example, assume container 1 currently contains gloves and container 2 currently contains bandages. If it is desired to switch these items so that container 1 contains bandages and container 2 contains gloves, the cumbersome processes described above would have to be followed, due to the hardwired and permanent nature of the take and return buttons and the current methodology.

Unfortunately, such reconfiguration and/or optimization, such as the steps of processes 200 and 300, are performed at the cabinet 100, rendering the cabinet unavailable to dispense medications to other users during such reconfiguration. For example, a pharmacy technician is often responsible to load 200 or reorganize 300 supplies in a cabinet 100, thereby effectively taking the cabinet 100 offline while nurses and other healthcare professionals who desire to use the cabinet 100 to dispense medications must wait. This causes undue delay in using the cabinets 100, especially in a hospital setting. In many cases, hospitals attempt to avoid this concern by leaving spaces in a cabinet 100 open or avoid reconfiguring the cabinet 100 altogether.

SUMMARY

Embodiments of the supply cabinet disclosed herein, which has particular use as a medication cabinet, provide mobile (e.g., wireless) terminals that can be quickly moved from one container in a cabinet to another container, and quickly associated and/or disassociated with a supply of items in the container. The mobile terminals are configured to transmit information indicating changes in quantity of the supply of the items, and can assist the cabinet's controller in determining the location of the items.

According to certain embodiments of the present disclosure, a system for tracking the quantity of an item is provided. The system includes a portable terminal, a client, and a cabinet. The portable terminal is configured to receive information indicating a change in the quantity of the item in a container. The portable terminal includes a unique identifier associated with the portable terminal, an input device configured to be actuated to indicate the change in the quantity of the item in the container, and a transceiver configured to transmit the information indicating the change in the quantity of the item. The client is configured to associate the portable terminal with the item based on the unique identifier. The client includes a transceiver configured to receive the information indicating the change in the quantity of the item from the portable terminal, and transmit the information. The cabinet includes the container configured to store the item, and a controller configured to change a value indicating a quantity of the item based on the information transmitted from the client.

According to other embodiments of the present disclosure, a system for tracking the quantity of an item is disclosed. The system includes a portable terminal configured to receive information indicating a change in the quantity of the item in a container. The portable terminal includes a unique identifier associated with the portable terminal, an input device configured to be actuated to indicate a change in the quantity of the item in the container, and a transceiver configured to transmit the information indicating the change in the quantity of the item.

According to certain aspects of the present disclosure, a method for tracking the quantity of an item is disclosed. The method includes receiving information from a portable terminal coupled to a first terminal location in a cabinet, the information indicating a change in the quantity. The method also includes associating the information with an item in a container of the cabinet based on a unique identifier associated with the portable terminal, and receiving information from the portable terminal at a second terminal location in a cabinet, the information indicating a change in the quantity of the same item.

BRIEF DESCRIPTION OF THE DRAWINGS

The accompanying drawings of the prior art are included to provide further understanding and are incorporated in and constitute a part of this specification. In the prior art drawings.

Figure 1:
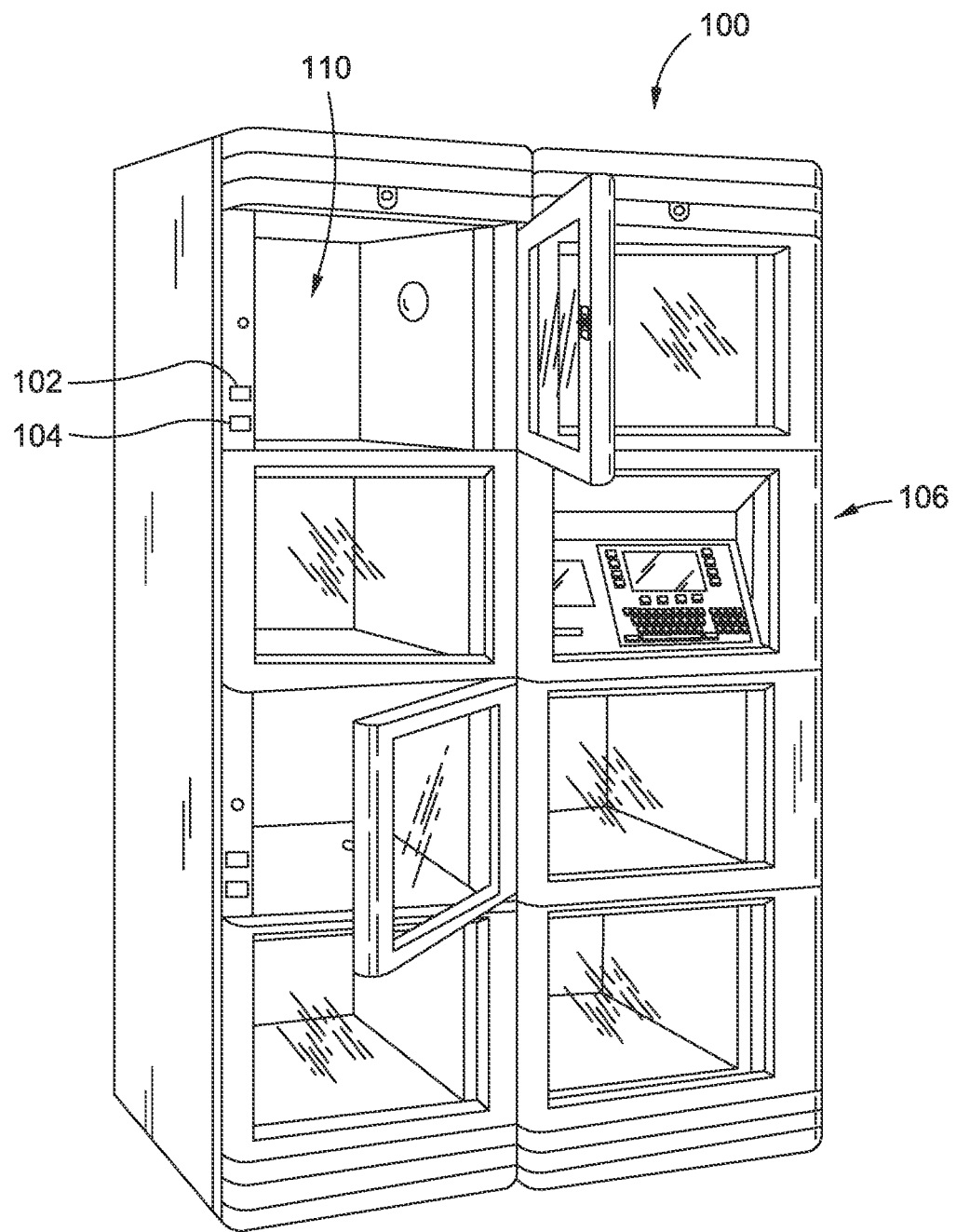
FIG. 1 illustrates a medication dispensing cabinet according to the prior art.

The accompanying drawings, which are included to provide further understanding and are incorporated in and constitute a part of this specification, illustrate disclosed embodiments and together with the description serve to explain the principles of the disclosed embodiments. In the drawings of the disclosed embodiments:

FIG. 4A illustrates a terminal and an association station according to certain embodiments.

FIG. 4B illustrates a rear-view of the terminal of FIG. 4A in the direction of arrow IV from FIG. 4A.

FIG. 5 illustrates a dispensing station including two terminals and the association station of FIGS. 4A-4B, according to certain embodiments.

Figure 6:
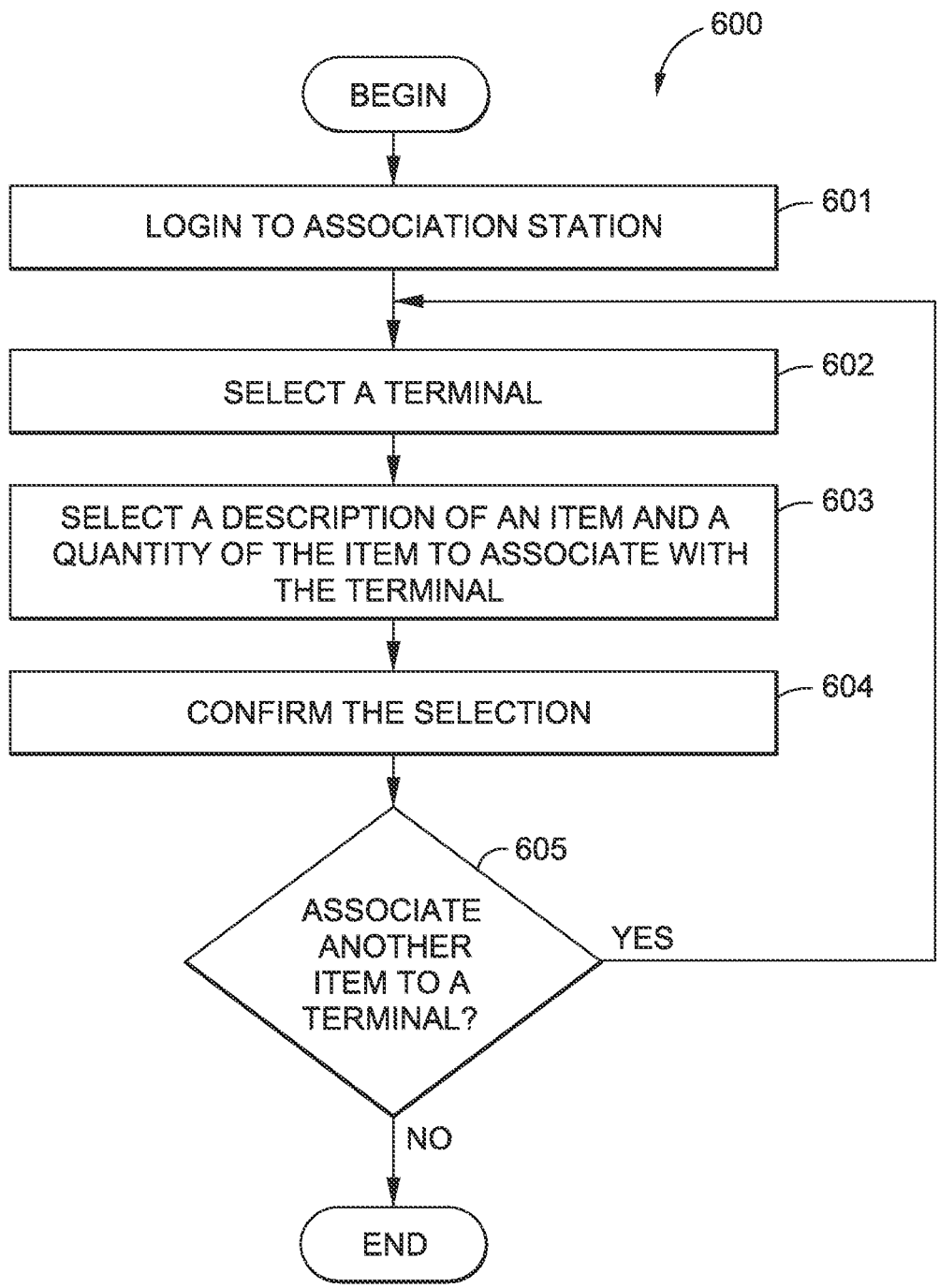

FIG. 6 illustrates a process for associating a supply of items with the terminal of FIG. 4A, according to certain embodiments.

Figure 7:
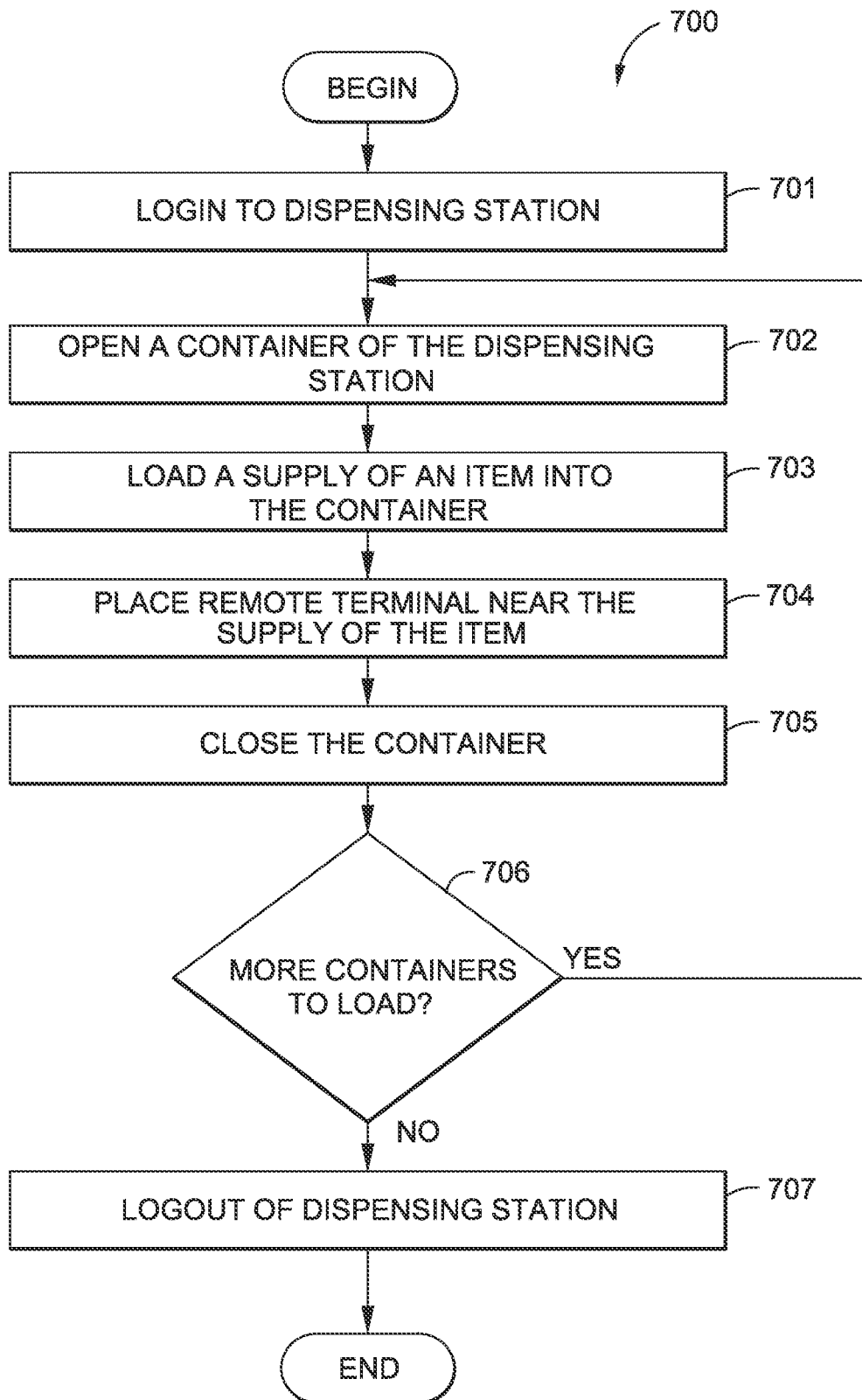

FIG. 7 illustrates a process for loading a supply of items in the dispensing station of FIG. 5, according to certain embodiments.

Figure 8:
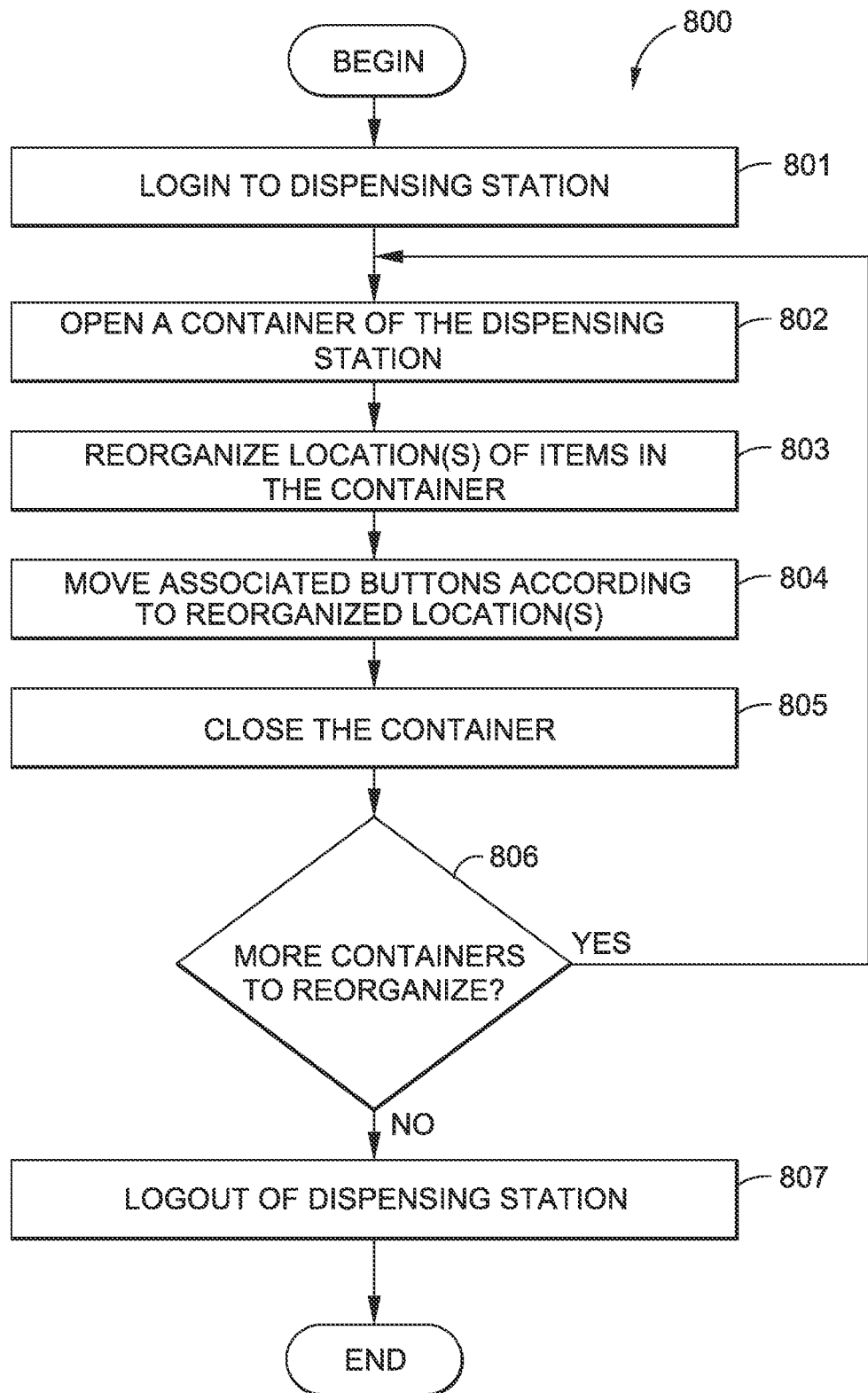

FIG. 8 illustrates a process for reorganizing a supply of items in the dispensing station of FIG. 5, according to certain embodiments.

Figure 9:
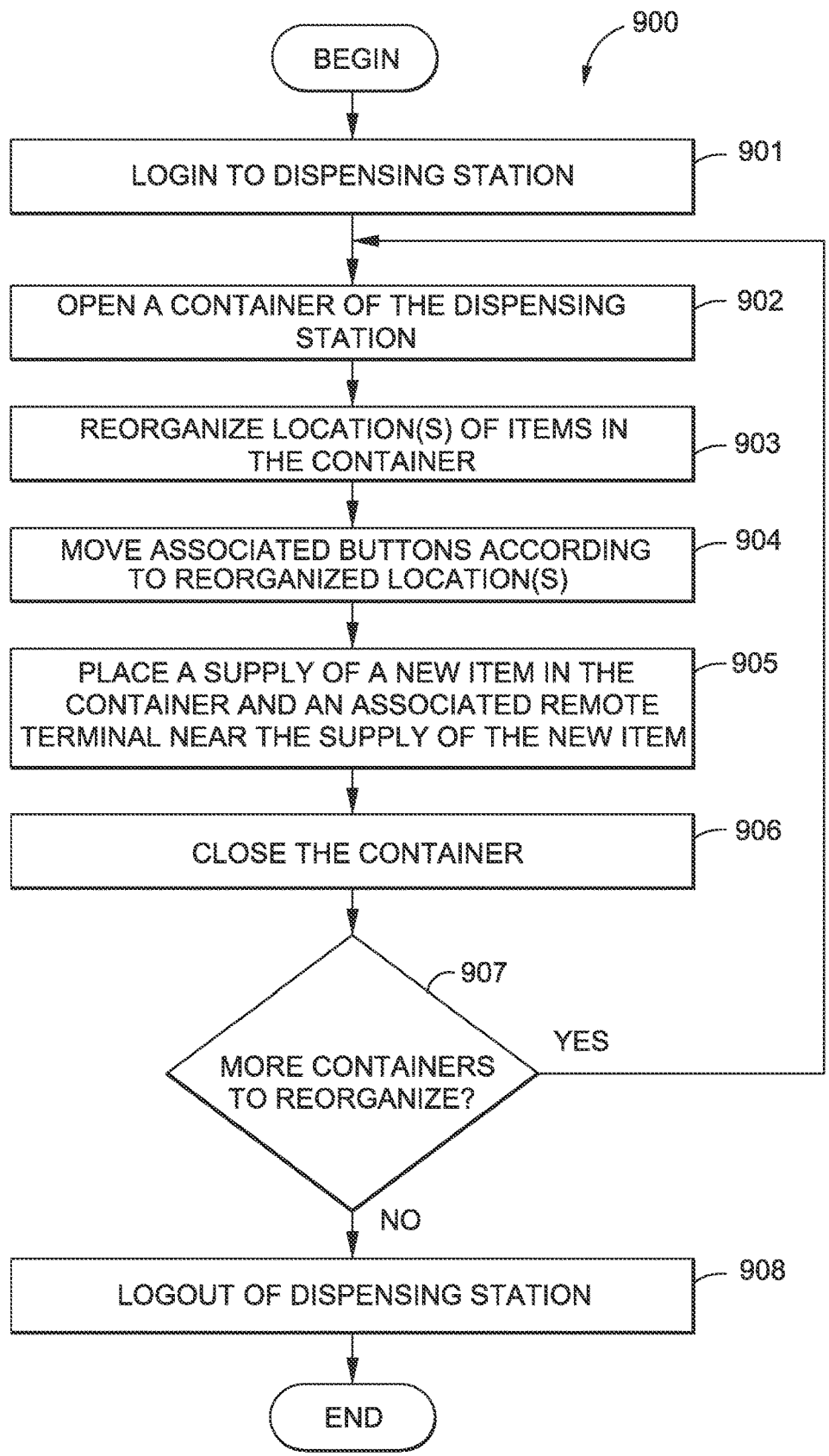

FIG. 9 illustrates a process for adding a new supply of items to the dispensing station of FIG. 4A, according to certain embodiments.

DETAILED DESCRIPTION

In the following detailed description, numerous specific details are set forth to provide a full understanding of the present disclosure. It will be obvious, however, to one ordinarily skilled in the art that the embodiments of the present disclosure may be practiced without some of these specific details. In other instances, well-known structures and techniques have not been shown in detail to avoid obscuring the disclosure. Furthermore, although the exemplary embodiments discussed herein refer to medical supply cabinets, the systems and methods disclosed herein are applicable to all types of supply cabinets.

FIG. 4A illustrates a terminal 410 (or "remote terminal" or "mobile terminal" or "button pair") and an association station 430 (or "client") according to certain embodiments. The terminal 410 is a mobile (e.g., wireless) terminal that can be quickly moved from one container in a cabinet to another container, and quickly associated and/or disassociated with a supply of items in the cabinet. The terminal 410 is detachable (e.g., not hardwired or permanently mounted), and readily removable and attachable to a cabinet as discussed below. The terminal 410 is configured to transmit information indicating a change in quantity of the supply of an item, and can assist in determining the location of the item.

The terminal 410 includes a unique identifier (not illustrated) associated with the terminal 410. The unique identifier can be, for example, an address, a bar code, or a radio frequency identification (RFID) tag. By having a unique identifier, the terminal 410 can distinguish itself from another terminal having another, different unique identifier.

The terminal 410 also includes one or several input devices, illustrated as buttons 412 and 414 in the embodiment of FIG. 4A, configured to be actuated to indicate a change in the quantity of an associated item. For example, in the illustrated embodiment, the "return" button 412 can be pressed by a user in order to indicate a decrease (e.g., by one) in the supply of the item, while the "take" button 414 can be pressed by the user in order to indicate an increase (e.g., by one) in the supply of the item. In certain embodiments, there may be only one input device configured to indicate a change in quantity of the item. In certain embodiments, there may be additional input devices associated with other actions, such as whether the terminal 410 is currently being used, to synchronize the terminal 410 with the association station 430, etc. Further, the actuation is not manual in certain embodiments, but is by other methods, such as by RFID recognition of placement or removal of an RFID tagged item.

An indication of the actuation (e.g., use) of the input devices 412 and 414 is provided by an indicator, illustrated as a light emitting diode (LED) 416 for the return button 412 and an LED for the take button 414. By providing an indication of the actuation of the input devices 412 and 414, the user is made aware of the functionality and/or change in status of the inventory. The terminal 410 also includes a transceiver 440 (schematically illustrated in phantom) configured to transmit information indicating the change in the quantity of the item. The transceiver 440 can connected to or otherwise include, for example, a central processing unit or computer configured to receive, store, and transmit information to a remote location, such as to the association station 430.

FIG. 4B illustrates a rear-view of the terminal 410 of FIG. 4A in the direction of arrow IV from FIG. 4A, according to certain embodiments. As illustrated, the terminal 410 includes mounting brackets 424 configured to couple the terminal 410 to another object, such as a dispensing cabinet. In certain embodiments, other types of mounting brackets 424 can be used, such as fasteners, couplers, magnets, etc. The terminal 410 also includes a mounting sensor 422 in certain embodiments. The mounting sensor 422 is configured to determine whether the terminal 410 is in use, such as by determining whether the terminal 410 is mounted to an object, such as the wall of a cabinet, or is being moved. In such cases, the mounting sensor 422 can be a proximity sensor or a contact sensor. The terminal 410 can be programmed to determine it is not in use if the mounting sensor 422 indicates the terminal 410 is not mounted, whereby the terminal 410 can decide to not transmit information from its transceiver and/or enter a power down mode. In certain embodiments, other actions may be taken by the terminal 410 if the mounting sensor 422 determines the terminal 410 is not in use. In certain embodiments, the terminal 410 can contain contact points through which the terminal 410 can communicate and receive power, such as by docking to embodiments of the cabinet discussed below. In certain embodiments, the terminal 410 contains its own power source (e.g., rechargeable batteries).

Association station 430 is configured to associate the portable terminal 410 with the item based on the unique identifier. The association station 430 can be, for example, a processing system that includes an input device (e.g., keyboard), output device (e.g., display), a processor, and memory. The association station 430 includes a transceiver 450 configured to receive the information indicating the change in the quantity of the item from the terminal 410, and transmit the information to the dispensing station 500 illustrated in FIG. 5.

Specifically, FIG. 5 illustrates a dispensing station 500 (or "medication cabinet" or "inventory-tracking device") including two terminals 410a and 410b and the association station 430 of FIGS. 4A-4B, according to certain embodiments. The dispensing station 500 includes a controller 506 that is configured to control access to containers 510 and 520 in the dispensing station 500, and track the quantity and location of the items in the containers 510 and 520. The controller can be, for example, a computer system that includes an input device (e.g., keyboard), output device (e.g., display), a processor, and memory. Association station 430 is configured to associate each of terminals 410a and 410b with different supplies of items based on the unique identifiers assigned to each of the terminals 410a and 410b. In certain embodiments, the association station 430 is separate from the controller 506 in order to provide the inventory tracking features of the mobile terminal 410 as discussed herein. In certain embodiments, the association station 430 can be included in or a part of the dispensing cabinet 500, and may be accessible through the controller 506 of the dispensing cabinet 500. However, it should be understood that in such embodiments, the terminal 410a and 410b remain mobile and are not hardwired to the dispensing station 500.

The association station 430 is further configured to communicate with a controller 506 included in the dispensing station 500, such as to indicate a change in the quantity of a supply of items and a location of the items. For example, if the take button of terminal 410a is pressed by a user, then terminal 410a transmits information to association station 430 indicating its take button has been pressed. The association station 430, which has associated a supply of items, for example, item A, with terminal 410a, receives the information from terminal 410a, and then transmits information to the controller 506 indicating item A has decreased by one. The controller 506 receives the information from the association station 430, and then updates its supply record of item A, decreasing the value by one. Furthermore, if only one container, container 510, of the association station 430 is open, then the controller 506 can also determine that item A associated with terminal 410a is in container 510, because no other containers of the dispensing station 500 are currently accessible. In certain embodiments, controller 506 interacts directly with terminal 410a (e.g., without association station 430), for example, to indicate a change in the quantity of a supply of items and a location of the items.

By way of another example, if initially both containers 510 and 520 are open, then terminal 410b is moved from container 510 to container 520 and container 510 is closed, and finally the take button of terminal 410b is pressed by a user, then the controller 506 can both (1) update its supply record of the item associated with terminal 410*b*, decreasing the value by one, and (2) update its location record of the item associated with terminal 410*b* to indicate the item's supply is now located in container 520, because no other containers of the dispensing station 500 are currently accessible other than container 520.

Figure 2:
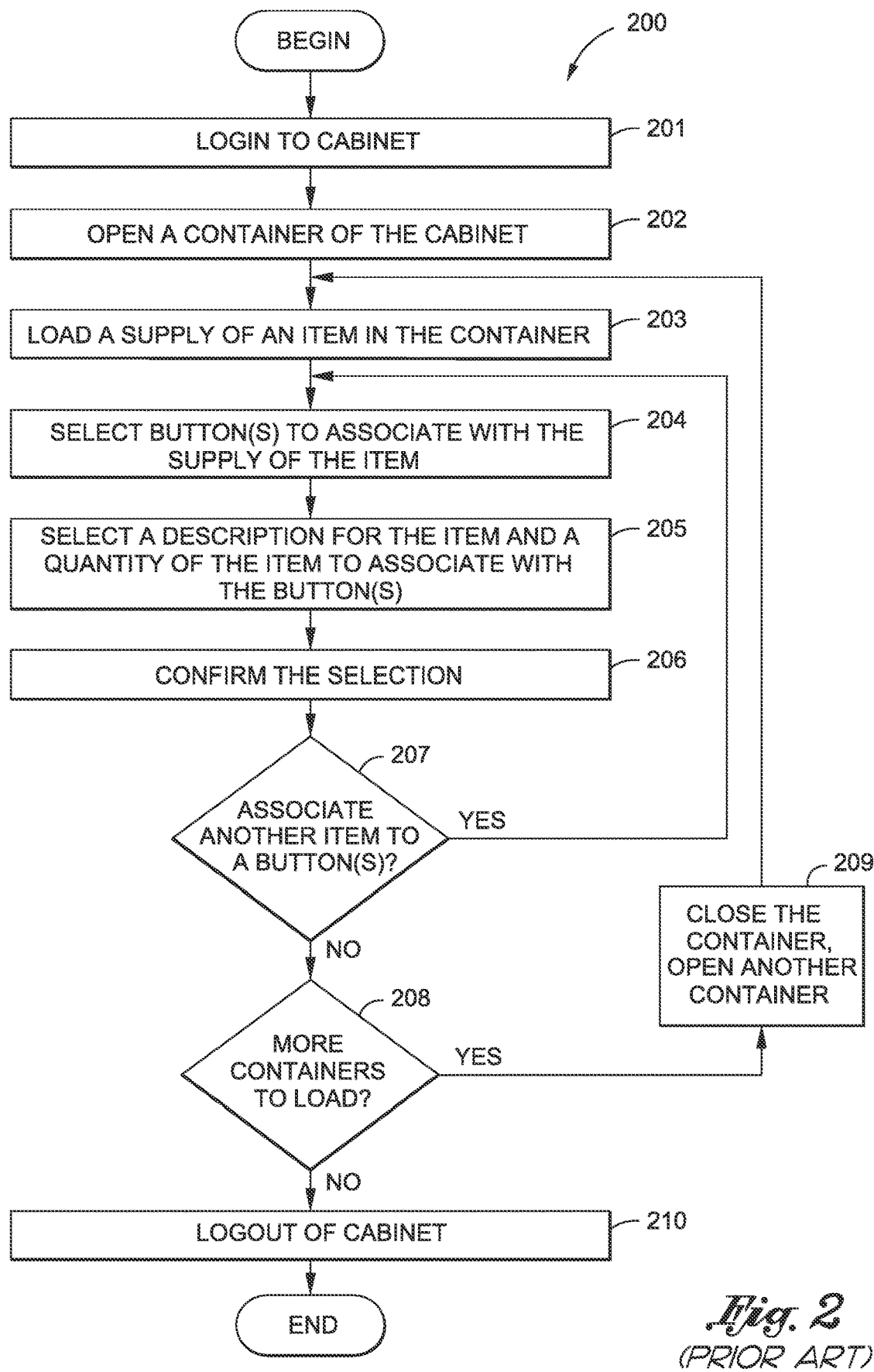
FIG. 2 illustrates a process for loading a supply of an item in the cabinet of FIG. 1, according to the prior art.

Unlike the prior art, in which an item is both associated with buttons 102 and 104 and loaded into a cabinet 100 in the same process (as illustrated in FIG. 2), resulting in significant downtime of the cabinet 100 on a hospital floor, the processes disclosed herein advantageously separate association of items with a terminal 410 (as described in FIG. 6) from loading the items and the terminal 410 in a dispensing station 500 (as described in FIG. 7), so that the association of the items with the terminal 410 can take place away from the hospital floor, reducing downtime of the dispensing station 500 to only the loading of items and the terminal into the dispensing station 500. In order to further increase efficiency, the terminal 410 may be associated with a supply of items when the items are packaged for delivery, such that a properly configured terminal 410 arrives each supply of items.

FIG. 6 illustrates a process 600 for associating a supply of items with the terminal 410 of FIG. 4A, according to certain embodiments. The process 600 can occur away from the location of the dispensing station 500 so that the dispensing station 500 can remain available to dispense medication and other items to users. The process 600 may be performed as many times as necessary to associate the required number of terminals 410 for supplies of items. The configuration created by the process 600, as well as the processes 700, 800, and 900 of FIGS. 7-9 may be stored in the terminal 410, the association station 430, the dispensing station 500, or another location.

The process 600 begins in step 601, where a user logs in to the association station 430, such as by providing authentication information. The authentication information can include a biometric identifier, a name and password, or other form of user identification known to those of skill in the art. In step 602, the user selects a terminal 410, and in step 603 selects a description of an item (e.g., "Atenolol 20 mg") and a quantity of the item (e.g., "50") to associate with the terminal 410. In step 604, the user confirms the selection of step 603. In decision step 605, if another terminal is to be associated with the supply of another item, the process 600 returns to step 602, otherwise the process 600 ends.

Having set forth in FIG. 6 a process 600 for associating a supply of items with the terminal 410 of FIG. 4A, an example will now be presented using the process 600 of FIG. 6 wherein a pharmacy technician associates the items Atenolol and Diazepam with the terminals 410*a* and 410*b* illustrated in FIG. 5. The process 600 begins in step 601, where the pharmacy technician logs in to the association station 430 using his user identification and password. In step 602, the pharmacy technician selects the terminal 410*a* in a container 510, and in step 603 enters the description "Atenolol 20 mg" and quantity "50" to associate with the terminal 410*a*. In step 604, the pharmacy technician confirms the selection of step 603. In decision step 605, the pharmacy technician chooses to associate another terminal with the supply of another item, and the process 600 returns to step 602. Returning to step 602, the pharmacy technician selects the terminal 410*b* in the container 510 (of FIG. 5), and in step 603 enters the description "Diazepam 10 mg" and quantity "50" to associate with the terminal 410*b*. In step 604, the pharmacy technician confirms the selection of step 603. In decision step 605, the pharmacy technician chooses not to associate another terminal with the supply of another item, and the process 600 ends.

FIG. 7 illustrates a process 700 for loading a supply of items in the dispensing station 500 of FIG. 5 with a terminal 410 configured using the process 600 of FIG. 6, according to certain embodiments. The process 700 begins in step 701, where a user logs in to the dispensing station 500, such as by providing authentication information. In step 702, the user opens a container 510 of the dispensing station 500, and then in step 703 loads a supply of an item into the container 510. In step 704, the terminal 410 configured in process 600 above for the supply of the item in the container 510 is placed near the supply of the item in the container 510, such as in front of the supply. The container 510 is closed in step 705. If in decision step 706 there are more containers to load, the process 700 returns to step 702, otherwise the user logs out of the dispensing station 500 in step 707 and the process 700 ends. From the standpoint of a dispensing station 500 user, the process 700 takes six steps, in comparison with the prior art process 200 illustrated in FIG. 2, which takes 9 steps. If the dispensing station 500 stores an average of 70 items, the process 700 disclosed herein saves 140 steps (saving 2 steps for each of 70 items), thereby providing an improvement in efficiency and time for the user.

Having set forth in FIG. 7 a process 700 for loading a supply of items in the dispensing station 500 with a terminal 410 configured using the process 600 of FIG. 6, an example will now be presented using the process 700 of FIG. 7 wherein a pharmacy technician loads the items Atenolol and Diazepam, and the terminals 410*a* and 410*b* into the dispensing station 500. The process 700 begins in step 701, where the pharmacy technician logs in to the dispensing station 500 using his fingerprint. The dispensing station 500 is thereby placed into a mode to recognize that the pharmacy technician intends to load or reorganize items in the dispensing station 500. In step 702, the pharmacy technician opens the container 510 of the dispensing station 500, and then in step 703 loads a supply of 50 Atenolol (50 mg/each) into the container 510. At this step, other containers in the dispensing station 500 may lock so that the dispensing station 500 can identify that any terminals 410 placed in the dispensing station 500 are in the opened container 510. In step 704, the pharmacy technician mounts the terminal 410*a* (configured in process 600 above for the supply of Atenolol) near the supply of Atenolol in a configuration that activates the mounting sensor 422 of the terminal 410*a*. The container 510 is closed in step 705. In decision step 706, the pharmacy technician decides there are more containers to load, and the process 700 returns to step 702. Returning to step 702, the pharmacy technician again opens the container 510 of the dispensing station 500, and then in step 703 loads a supply of 50 Diazepam (10 mg/each) into the container 510. In step 704, the pharmacy technician mounts the terminal 410*b* (configured in process 600 above for the supply of Diazepam) near the supply of Diazepam in a configuration that activates the mounting sensor 422 of the terminal 410*b*. The container 510 is closed in step 705. In decision step 706, the pharmacy technician decides there are no more containers to load, the pharmacy technician logs out of the dispensing station 500 in step 707, and the process 700 ends.

FIG. 8 illustrates a process 800 for reorganizing a supply of items in the dispensing station 500 of FIG. 5, according to certain embodiments. The process 800 begins in step 801, where a user logs in to the dispensing station 500, such as by providing authentication information. In step 802, the user opens a container 510 of the dispensing station 500, and then in step 803 reorganizes the locations of items in the container 510. In step 804, the user moves the terminals 410 associated with the items according to the reorganized location of the items, so that each terminal 410 associated with a supply of an item is proximal to the supply of the item. The container 510 is closed in step 805. If in decision step 806 there are more containers to reorganize, the process 800 returns to step 802, otherwise the user logs out of the dispensing station 500 in step 807 and the process 800 ends.

Figure 3:
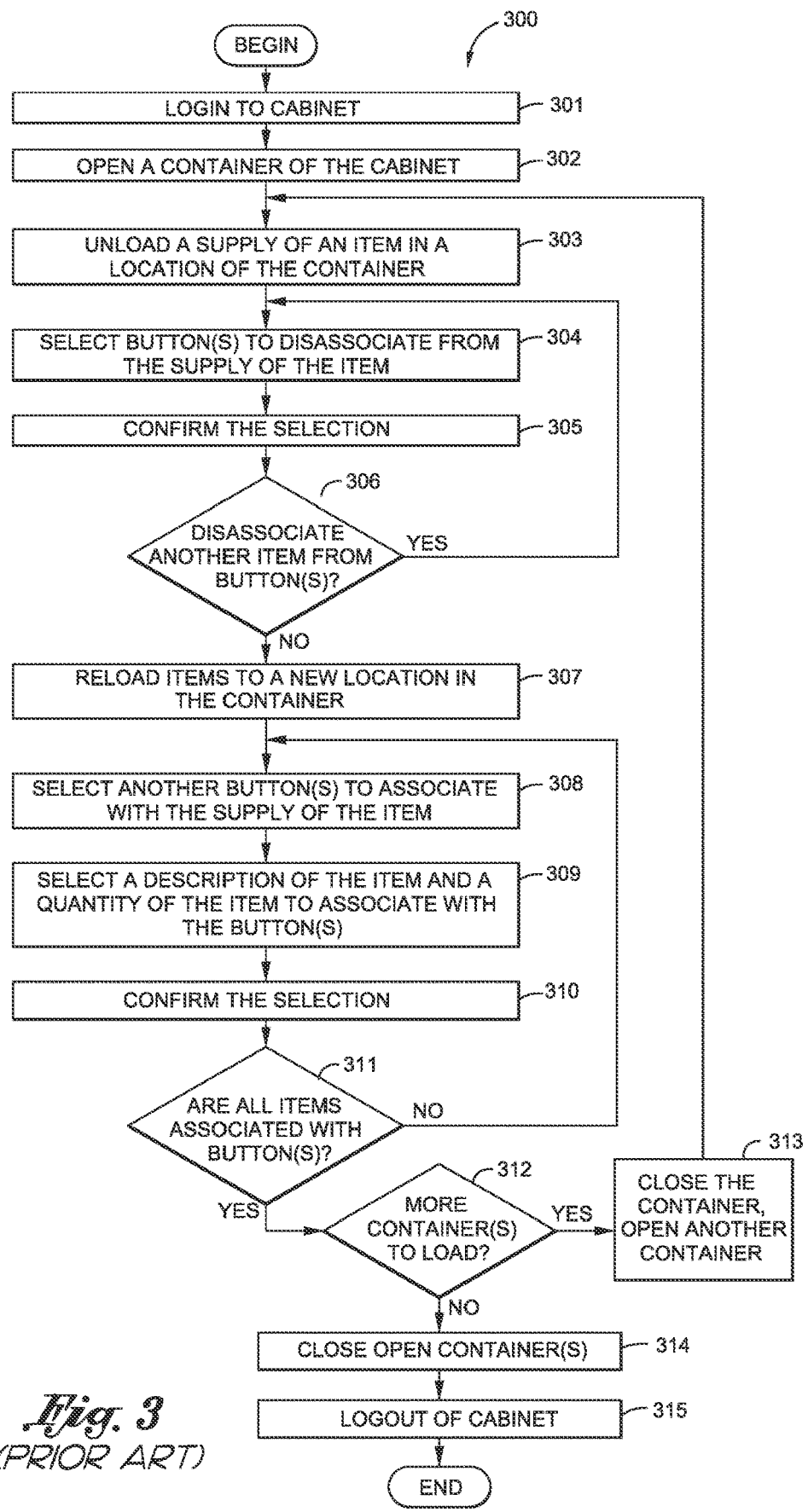
FIG. 3 illustrates a process for reorganizing a supply of items in the cabinet of FIG. 1, according to the prior art.

Unlike the prior art process 300 of FIG. 3, in which the user was required to disassociate a pair of buttons with an item and then re-associate a new pair of buttons with the item, in the process 800 disclosed herein the user simply needs to move the terminal 410 along with the item. The number of steps in process 800 is reduced by half (7 steps in process 800 versus 14 steps in process 300) compared to the prior art process 300 for reorganizing a supply of items.

Having set forth in FIG. 8 a process 800 for reorganizing a supply of items in the dispensing station 500 of FIG. 5, an example will now be presented using the process 800 of FIG. 8 wherein a pharmacy technician reorganizes the items Atenolol and Diazepam, and their associated terminals 410a and 410b, in the dispensing station 500. The process 800 begins in step 801, where the pharmacy technician logs in to the dispensing station 500 using his fingerprint. The dispensing station 500 is thereby placed into a mode to recognize that the pharmacy technician intends to load or reorganize items in the dispensing station 500. In step 802, the pharmacy technician opens the container 510 of the dispensing station 500 containing the supplies of Atenolol and Diazepam, and then in step 803 reorganizes the container 510 by removing the supply of Diazepam from the container 510. At step 802, other containers in the dispensing station 500 may lock so that the dispensing station 500 can identify that any terminals reorganized in the dispensing station 500 are in the opened container 510. In step 804, the pharmacy technician removes the terminal 410b associated with the supply of Diazepam. The container 510 is closed in step 805. In decision step 806, the pharmacy technician decides there are more containers to reorganize because he wants to add the supply of Diazepam to another container 520 (illustrated in FIG. 5) in the dispensing station 500, so the process 800 returns to step 802. Returning to step 802, the pharmacy technician opens the other container 520 of the dispensing station 500, and in step 803 reorganizes the container 520 by loading the supply of Diazepam into the container 520. In step 804, the pharmacy technician mounts the terminal 410b associated with the supply of Diazepam into the container 520 in a configuration that activates the mounting sensor 422 of the terminal 410b. The pharmacy technician may optionally press both the take button 414 and the return button 412 of the terminal 410b together to indicate to the controller 506 of the dispensing station (as discussed above) that the supply of Diazepam is now located in container 520, not container 510. The container 520 is closed in step 805. In decision step 806, the pharmacy technician decides there are no more containers to reorganize, the pharmacy technician logs out of the dispensing station 500 in step 807, and the process 800 ends.

FIG. 9 illustrates a process for adding a new supply of items to the dispensing station 500 of FIG. 5, according to certain embodiments. The process 900 begins in step 901, where a user logs in to the dispensing station 500, such as by providing authentication information. In step 902, the user opens a container 510 of the dispensing station 500, and then in step 903 reorganizes the locations of items in the container 510. In step 904, the user moves the terminals 410 associated with the items according to the reorganized location of the items, so that each terminal 410 associated with a supply of an item is proximal to the supply of the item. In step 905, a supply for a new item is placed in the open container 510, and a remote terminal 410 associated with the supply for the new item is placed in proximity to the supply in container 510. The container 510 is closed in step 906. If in decision step 906 there are more containers to reorganize or to which new items are to be added, the process 900 returns to step 902, otherwise the user logs out of the dispensing station 500 in step 908 and the process 900 ends. As can be seen from the disclosed process 900 for adding a new item to a container 510, only one new step, step 905, is added as compared to the disclosed process 800 for reorganizing items in a container 510.

Having set forth in FIG. 9 a process 900 for adding a new supply of items to the dispensing station 500 of FIG. 5, an example will now be presented using the process 900 of FIG. 9 wherein a pharmacy technician adds the item Acebutolol and an associated terminal 410 in the dispensing station 500. The process 900 begins in step 901, where the pharmacy technician logs in to the dispensing station 500 using his fingerprint. The dispensing station 500 is thereby placed into a mode to recognize that the pharmacy technician intends to load or reorganize items in the dispensing station 500. In step 902, the pharmacy technician opens the container 510 of the dispensing station 500, and then in step 903 reorganizes the locations of items in the container 510 to create space for the new item, Acebutolol. At step 902, other containers in the dispensing station 500 may lock so that the dispensing station 500 can identify that any terminals reorganized in the dispensing station 500 are in the opened container 510. In step 904, the pharmacy technician moves the terminals 410 associated with the items according to the reorganized location of the items, so that each terminal 410 associated with a supply of an item is proximal to the supply of the item in a configuration that activates each mounting sensor 422 of the terminals 410. In step 905, a supply for Acebutolol is placed in the open container 510, and a remote terminal 410 associated with the supply of Acebutolol is placed near the supply in the container 510. The container 510 is closed in step 906. The pharmacy technician decides there are no more containers to reorganize in decision step 906, the pharmacy technician logs out of the dispensing station 500 in step 908, and the process 900 ends.

The embodiments of the present disclosure provide a supply cabinet that includes mobile (e.g., wireless) terminals that can be quickly moved from one container in the cabinet to another container, and quickly associated and/or disassociated with a supply of items in the container. The mobile terminals are configured to transmit information indicating changes in quantity of the supply of the items, and can assist the cabinet's controller in determining the location of the items.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A system, comprising:
   a first mobile terminal comprising transceiver equipment for communicating with a client device, the first mobile terminal configured to, when associated with an electronic storage cabinet having a plurality of containers, detect, using radio-frequency identification (RFID) recognition, a respective item unit being moved from or to a respective container of the plurality of containers based on detecting an RFID tag affixed to the respective item unit, and to transmit an output comprising an indication of the respective item unit being moved from or to the respective container; and a non-transitory computer-readable medium having instructions thereon that, when executed by an item association station, cause the item association station to perform operations comprising:

associating the first mobile terminal with a first item type stored in the electronic storage cabinet;

receiving, from the transceiver equipment of the first mobile terminal, the output indicating the first item type being moved from or to a first container of the plurality of containers;

electronically obtaining, from a controller of the electronic storage cabinet, in connection with receiving the output, an access status indicating which of the plurality of containers is open and which of the plurality of containers is closed;

determining a new location for the respective item unit based on the received output and the electronically obtained access status; and causing, responsive to determining the new location, a supply record associated with the first item type and the first container of the electronic storage cabinet to be updated to reflect a change to a first amount of the first item type stored in the first container.

2. The system of claim 1, wherein the access status indicates which of the plurality of containers is open and which of the plurality of containers is closed by indicating that a respective container associated with the new location is the only currently accessible container of the plurality of containers.

3. The system of claim 1, wherein determining the new location for the respective item unit based on the access status of the plurality of containers comprises determining a prior container location of the respective item unit and a new container location of the respective item unit.

4. The system of claim 1, wherein causing the supply record to be updated comprises causing the supply record to be updated to reflect that a first amount of the first item type decreased in the first container of the plurality of containers, and that a second amount of the first item type increased in a second container of the plurality of containers.

5. The system of claim 1, wherein the electronic storage cabinet is a medication dispensing cabinet and the first item type is a medication type.

6. The system of claim 1, wherein the operations further comprise:
determining, while the first container and a second container of the plurality of containers are open, that the first mobile terminal is placed at the first container and then moved to a second container of the plurality of containers.

7. The system of claim 1, wherein first mobile terminal being configured to transmit the output comprises the first mobile terminal being configured to transmit the output based on a sensor associated with the first mobile terminal indicating that the first mobile terminal is in use with the electronic storage cabinet.

8. The system of claim 1, wherein the operations further comprise:

associating a second mobile terminal with a second item type and the electronic storage cabinet;

receiving, from the second mobile terminal, a second indication of a second item unit of the second item type being moved;

determining a container location for the second item unit based on an access status of one or more respective containers of the electronic storage cabinet and receiving the indication of the respective item unit being moved from the second mobile terminal; and causing, responsive to determining the container location, a supply record associated with the second item type and a second container of the electronic storage cabinet to be updated to reflect a change to a second amount of the second item type stored in the second container.

9. A method, comprising:

associating a first mobile terminal with an electronic storage cabinet having a plurality of containers, the first mobile terminal comprising transceiver equipment for communicating with a client device, the first mobile terminal configured to detect, using radio-frequency identification (RFID) recognition, a respective item unit being moved from or to a respective container of the plurality of containers based on detecting an RFID tag affixed to the respective item unit, and to transmit an output comprising an indication of the respective item unit being moved from or to the respective container;

associating, using an association station, the first mobile terminal with a first item type stored in the electronic storage cabinet;

receiving, from the transceiver equipment of the first mobile terminal, the output indicating the first item type being moved from or to a first container of the plurality of containers;

electronically obtaining, from a controller of the electronic storage cabinet, in connection with receiving the output, an access status indicating which of the plurality of containers is open and which of the plurality of containers is closed;

determining a new location for the respective item unit based on the received output and the electronically obtained access status; and causing, responsive to determining the new location, a supply record associated with the first item type and the first container of the electronic storage cabinet to be updated to reflect a change to a first amount of the first item type stored in the first container.

10. The method of claim 9, wherein the access status indicates which of the plurality of containers is open and which of the plurality of containers is closed by indicating that a respective container associated with the new location is the only currently accessible container of the plurality of containers.

11. The method of claim 9, wherein causing the supply record to be updated comprises causing the supply record to be updated to reflect that a first amount of the first item type decreased in the first container of the plurality of containers, and that a second amount of the first item type increased in a second container of the plurality of containers.

12. The method of claim 9, wherein determining the new location for the respective item unit based on the access status of the plurality of containers comprises determining a prior container location of the respective item unit and a new container location of the respective item unit.

13. The method of claim 9, wherein the electronic storage cabinet is a medication dispensing cabinet and the first item type is a medication type.

14. The method of claim 9, further comprising:
receiving, from a sensor associated with the first mobile terminal, an indication that the first mobile terminal is in use with the electronic storage cabinet; and
transmitting the output based on a sensor associated with the first mobile terminal indicating that the first mobile terminal is in use with the electronic storage cabinet.

15. The method of claim 9, wherein the method further comprise:
associating a second mobile terminal with a second item type and the electronic storage cabinet;
receiving, from the second mobile terminal, a second indication of a second item unit of the second item type being moved;
determining a container location for the second item unit based on an access status of one or more respective containers of the electronic storage cabinet and receiving the indication of the respective item unit being moved from the second mobile terminal; and
causing, responsive to determining the container location, a supply record associated with the second item type and a second container of the electronic storage cabinet to be updated to reflect a change to a second amount of the second item type stored in the second container.

16. A non-transitory computer-readable medium comprising instructions stored thereon that, when executed by one or more processors, cause the one or more processors to perform operations, comprising:
associating a mobile terminal with an electronic storage cabinet having a plurality of containers, the mobile terminal comprising transceiver equipment for communicating with a client device, the mobile terminal configured to detect, using radio-frequency identification (RFID) recognition, a respective item unit being moved from or to a respective container of the plurality of containers based on detecting an RFID tag affixed to the respective item unit, and to transmit an output comprising an indication of the respective item unit being moved from or to the respective container;
associating, using an association station, the mobile terminal with an item type stored in the electronic storage cabinet;
receiving, from the transceiver equipment of the mobile terminal, the output indicating the item type being moved from or to a first container of the plurality of containers;
electronically obtaining, from a controller of the electronic storage cabinet, in connection with receiving the output, an access status indicating which of the plurality of containers is open and which of the plurality of containers is closed;
determining a new location for the respective item unit based on the received output and the electronically obtained access status; and
causing, responsive to determining the new location, a supply record associated with the item type and the first container of the electronic storage cabinet to be updated to reflect a change to a first amount of the item type stored in the first container.

17. The non-transitory computer-readable medium of claim 16, wherein the access status indicates which of the plurality of containers is open and which of the plurality of containers is closed by indicating that a respective container associated with the new location is the only currently accessible container of the plurality of containers.

18. The non-transitory computer-readable medium of claim 16, wherein causing the supply record to be updated comprises causing the supply record to be updated to reflect that a first amount of the item type decreased in the first container of the plurality of containers, and that a second amount of the item type increased in a second container of the plurality of containers.

19. The non-transitory computer-readable medium of claim 16, wherein determining the new location for the respective item unit based on the access status of the plurality of containers comprises determining a prior container location of the respective item unit and a new container location of the respective item unit.

20. The non-transitory computer-readable medium of claim 16, the operations further comprising:
receiving, from a sensor associated with the mobile terminal, an indication that the mobile terminal is in use with the electronic storage cabinet; and
transmitting the output based on a sensor associated with the mobile terminal indicating that the mobile terminal is in use with the electronic storage cabinet.

\* \* \* \* \*